United States Patent [19]

Bilstad et al.

[11] 4,333,016

[45] Jun. 1, 1982

[54] LIQUID PRESENCE DETECTOR

[75] Inventors: Arnold C. Bilstad, Deerfield; Richard I. Brown, Northbrook, both of Ill.

[73] Assignee: Baxter Travenol Laboratories, Inc., Deerfield, Ill.

[21] Appl. No.: 127,553

[22] Filed: Mar. 6, 1980

[51] Int. Cl.³ .......................................... G01N 15/06
[52] U.S. Cl. .............................. 250/577; 250/214 R
[58] Field of Search .............. 250/577, 573, 574, 575, 250/210, 564, 565, 214 R, 214 A; 356/436, 441, 442

[56] References Cited

U.S. PATENT DOCUMENTS

| | | | |
|---|---|---|---|
| 2,980,802 | 4/1961 | Bracey et al. | 250/577 |
| 3,549,893 | 12/1970 | Gibbs | 250/577 |
| 3,632,211 | 1/1972 | Sedivy et al. | 250/573 |
| 3,912,393 | 10/1975 | Hossom et al. | 250/574 |
| 4,232,967 | 11/1980 | Grachev et al. | 250/574 |

Primary Examiner—David C. Nelms
Attorney, Agent, or Firm—Paul C. Flattery; George H. Gerstman; Eugene M. Cummings

[57] ABSTRACT

A liquid presence detector having a light-transmissive chamber for the liquid to be detected. A light emitting diode is positioned outside of the chamber for transmitting light through the chamber and a photosensitive transistor is positioned for receiving the light that has been transmitted through the chamber. The light emitting diode is located at a distance from the chamber that is equal to the focal point of a lens that is created by the chamber and liquid when the liquid is present. The photosensitive transistor output voltage is compared with a reference voltage and an output signal is provided in response to a predetermined difference between the detector output voltage and the reference voltage.

5 Claims, 4 Drawing Figures

LIQUID PRESENCE DETECTOR

BACKGROUND OF THE INVENTION

The present invention concerns a novel liquid presence detector.

In certain applications it is essential that the presence of a colorless liquid be detected. For example, in blood processing, including blood fractionation, a colorless anticoagulant supply is often fed during the processing of the blood. The absence of the anticoagulant during the blood processing may cause serious consequences and for that reason it is important that an effective detector be provided for detecting the presence of the anticoagulant. It is to be understood, however, that the detection of the presence of anticoagulant is but one of the many uses of the liquid presence detector to be described herein.

An object of the present invention is to provide a liquid presence detector that is capable of detecting accurately the presence or absence of a colorless liquid.

Another object of the present invention is to provide a liquid presence detector that is simple in construction and is efficient to manufacture.

Another object of the present invention is to provide a liquid presence detector that is reliable and requires a relatively small number of parts.

A further object of the present invention is to provide a liquid presence detector that includes safety provisions in the event of component failure.

Other objects and advantages of the present invention will become apparent as the description proceeds.

SUMMARY OF THE INVENTION

In accordance with the present invention, a liquid presence detector is provided which comprises a light-transmissive chamber for the liquid to be detected. A light source is positioned outside the chamber for transmitting light through the chamber and a light detector is provided for receiving the light that has been transmitted through the chamber. The light source is located at a distance from the chamber that is equal to the focal point of a lens that is created by the chamber and liquid when the liquid is present.

In the illustrative embodiment, a reference voltage level is provided. The detector output voltage is compared with the reference voltage level and an output signal is provided in response to a predetermined difference between the reference voltage and the detector output voltage.

In the illustrative embodiment, the light-transmissive chamber comprises a flexible plastic tube, the light source comprises a light emitting diode and the light detector comprises a photosensitive transistor. A potentiometer is coupled to the light emitting diode for calibrating the detector output voltage.

In the illustrative embodiment, four comparators are provided, and the reference voltage is provided by a voltage divider. A first point on the voltage divider is coupled to an input of the first comparator, a second point on the voltage divider is coupled to an input of the second comparator, and a third point on the voltage divider is coupled to inputs of the third and fourth comparators. The detector output is coupled to the other inputs of the four comparators. In this manner, an output signal is provided by at least one of the comparators when the detector output voltage differs a predetermined amount from the reference voltage.

A more detailed explanation of the invention is provided in the following description and claims, and is illustrated in the accompanying drawings.

DETAILED DESCRIPTION OF THE ILLUSTRATIVE EMBODIMENT

Figure 1:
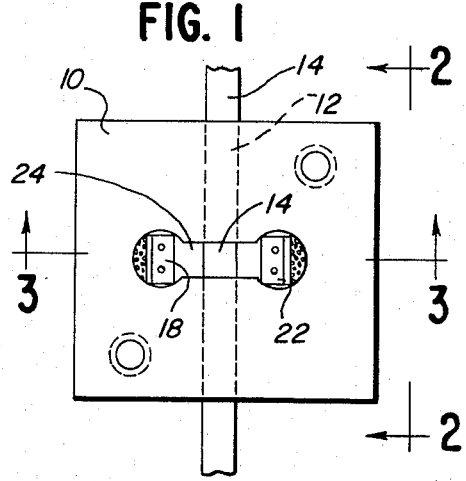
FIG. 1 is a rear view of a liquid presence detector assembly constructed in accordance with the principles of the present invention.
Figure 2:
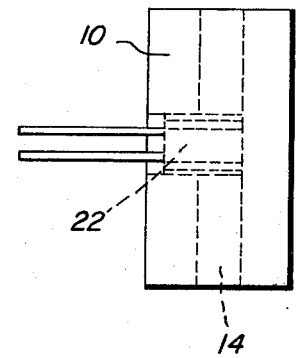
FIG. 2 is a right-side view thereof, taken along the plane of the lines 2—2 of FIG. 1.
Figure 3:
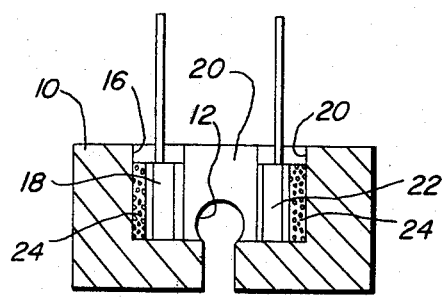
FIG. 3 is a cross-sectional view of the liquid detector assembly of FIG. 1, taken along the plane of the lines 3—3 of FIG. 1.

Referring first to FIGS. 1–3, the liquid presence detector assembly includes a housing 10 defining a slot 12 for receiving a transparent chamber 14 through which the liquid to be detected flows. In the illustrative embodiment, transparent chamber 14 comprises flexible plastic tubing which is pressure-fitted into slot 12. Thus slot 12 is dimensioned to receive the plastic tubing 14 with a snug fit.

An opening 16 is provided for receiving a light source 18 in the form of a light emitting diode (LED) and an opening 20 is provided for receiving a light detector 22 in the form of a photosensitive transistor. LED 18 and photosensitive transistor 22 may be obtained in the form of a single package, which is sold by General Electric Company under component No. H23BL. LED 18 and phototransistor 22 are positioned in the openings 16, 20, respectively, as illustrated in FIG. 3, on opposite sides of slot 12, and the space remaining in the openings 16, 20 is filled with an epoxy resin 24. As illustrated in FIGS. 1 and 3, openings 16 and 20 are contiguous to provide an air space 24 separating the light source 18 from chamber 14 and separating the detector 22 from chamber 14.

A feature of the present invention is the location of LED 18 at a distance from chamber 14 that is equal to the focal point of a lens that is created by chamber 14 and the liquid therein when the liquid is present in the chamber.

Figure 4:
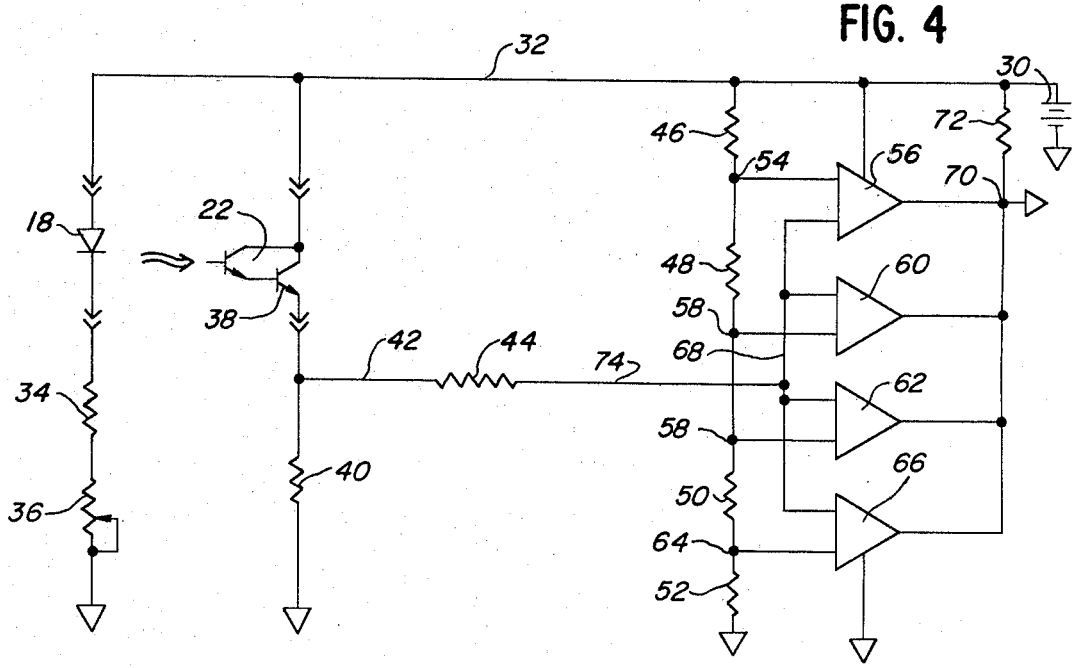
FIG. 4 is a schematic circuit diagram of a liquid presence detector circuit in accordance with the principles of the present invention.

Referring now to FIG. 4, a source 30 of direct current is coupled via line 32 to LED 18 and photosensitive transistor 22 (which is in the form of a Darlington pair). LED 18 is coupled in series with a resistor 34 and a potentiometer 36, while the emitter 38 of transistor pair 22 is coupled to ground via resistor 40 and is coupled to a comparator circuit via line 42 and resistor 44.

A voltage divider is provided including resistor 46, resistor 48, resistor 50 and resistor 52. A point 54 on the voltage divider between resistor 46 and 48 is connected to an input of comparator 56, a point 58 on the voltage divider between resistor 48 and resistor 50 is connected to an input of each of comparators 60 and 62, and a point 64 on the voltage divider between resistors 50 and 52 is connected to an input of comparator 66. The other inputs of comparators 56, 60, 62 and 66 are connected to line 42 via line 68. The outputs of comparators 56, 60, 62 and 66 are coupled to a common output point 70. A resistor 72 is connected between output point 70 and line 32.

Although no limitation is intended, the following is a specific example of parameters that have been found to provide a satisfactory circuit:

| Component | Value or Model No. |
|---|---|
| 18, 22 | GE H23BL |
| Resistor 34 | 510 ohms |
| Potentiometer 36 | 0–1K |
| Resistor 40 | 10K |
| Resistor 44 | 10K |
| Resistor 46 | 4.99K |
| Resistor 48 | 10K |
| Resistor 50 | 10K |
| Resistor 52 | 4.99K |
| Comparators 56, 60, 62 and 66 | LM339A |
| Resistor 72 | 10K |
| DC supply 30 | 15 volts |

In the operation of the FIG. 4 circuit, potentiometer 36 is adjusted with liquid being present in the chamber so that there is a voltage at point 74 of nine volts. With source 30 providing 15 volts, it can be seen that point 54 will be approximately 12.5 volts, point 58 will be approximately 7.5 volts and point 64 will be approximately 2.5 volts. The system is thus operative to provide a low output signal at point 70 if the voltage at point 74 is less than 7.5 volts or is greater than 12.5 volts. Thus if the voltage at point 74 is less than 7.5 volts, comparators 60 and 62 will provide a low output signal while if the voltage at point 74 is greater than 12.5 volts, comparator 56 will provide a low output signal. Comparators 60 and 62 are duplicates of each other, for safety purposes. Comparator 66 is also provided for safety purposes, in the event that comparators 60 or 62 do not operate and the voltage at point 74 is below 2.5 volts. In such event, comparator 66 will provide a low output signal. Output 70 may be connected to suitable circuitry as is well-known in the art, for further processing, such as terminating operation of the system.

Although an illustrative embodiment of the invention has been shown and described, it is to be understood that various modifications and substitutions may be made by those skilled in the art without departing from the novel spirit and scope of the present invention.

What is claimed is:

1. A liquid presence detector for detecting the absence of fluid in a fluid chamber, comprising:
a radiation source positioned outside the chamber for transmitting radiation through the chamber, the magnitude of radiation transmitted through the chamber being dependent on the presence of fluid therein;
a radiation detector for receiving radiation transmitted through the chamber and producing an output signal having a level dependent on the magnitude thereof,
said detector output signal having a normal operating range extending from a predetermined maximum signal level to a predetermined minimum signal level;
first comparison means for comparing the detector output signal level with a first reference signal level to develop an output when said output signal level exceeds a first predetermined threshold level between said maximum and minimum detector output levels;
second comparison means for comparing the detector output signal level with a second reference signal level to develop an output when said output level exceeds a second predetermined threshold level above said maximum signal level; and
output circuit means responsive to outputs from either said first or second comparison means for providing an alarm output signal.

2. A liquid presence detector as defined in claim 1 wherein said radiation source comprises a light source and said radiation detector comprises a light detector.

3. A liquid presence detector as defined in claim 1 wherein said first predetermined threshold level corresponds to the transition of said detector output signal between fluid presence and fluid absence in the chamber.

4. A liquid presence detector as defined in claim 1 including third comparison means for comparing the detector output signal with a third predetermined reference level to develop an output when said output level falls below a third predetermined threshold level below said minimum detector output level, and wherein said output circuit means is responsive to the output of said third comparison means.

5. A liquid presence detector for detecting the absence of fluid in a fluid chamber, comprising:
a light source positioned outside the chamber for transmitting light through the chamber, the magnitude of light transmitted through the chamber being dependent on the presence of fluid therein;
a light detector for receiving light transmitted through the chamber and producing an output signal having a level dependent on the magnitude thereof;
said detector output signal having a normal operating range extending from a determined maximum signal level to a predetermined minimum signal level;
first comparison means for comparing the detector output signal level with a first reference signal level to develop an output when said output signal level exceeds a first predetermined threshold level between said maximum and minimum detector output levels corresponding to the transition of said detector output signal between fluid presence and fluid absence in the chamber;
second comparison means for comparing the detector output signal level with a second reference signal level to develop an output when said output level exceeds a second predetermined threshold level above said maximum signal level;
third comparison means for comparing the detector output signal with a third predetermined reference level to develop an output when said output level falls below a third predetermined threshold level below said minimum detector output level; and
output circuit means responsive to outputs from either said first, second or third comparison means for providing an alarm output signal.

* * * * *